(12) United States Patent
Parihar et al.

(10) Patent No.: US 10,485,580 B2
(45) Date of Patent: Nov. 26, 2019

(54) TROCAR WITH OBLIQUE NEEDLE INSERTION PORT AND COPLANAR STOPCOCK

(71) Applicant: ETHICON LLC, Guaynabo, PR (US)

(72) Inventors: Shailendra K. Parihar, Mason, OH (US); Jason L. Harris, Lebanon, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 225 days.

(21) Appl. No.: 15/637,688

(22) Filed: Jun. 29, 2017

(65) Prior Publication Data

US 2019/0000503 A1 Jan. 3, 2019

(51) Int. Cl.
*A61B 17/04* (2006.01)
*A61B 17/34* (2006.01)
(Continued)

(52) U.S. Cl.
CPC ...... *A61B 17/3421* (2013.01); *A61B 17/0482* (2013.01); *A61B 17/06109* (2013.01); *A61B 17/3403* (2013.01); *A61B 17/3417* (2013.01); *A61B 17/0483* (2013.01); *A61B 17/3462* (2013.01); *A61B 17/3474* (2013.01);
(Continued)

(58) Field of Classification Search
CPC . A61B 17/04; A61B 17/0482; A61B 17/0483; A61B 17/0493; A61B 17/34; A61B 17/3403; A61B 17/3417; A61B 17/3419; A61B 17/3421; A61B 17/3423; A61B 17/3462; A61B 17/3474; A61B 2017/00637; A61B 2017/3445;
(Continued)

(56) References Cited

U.S. PATENT DOCUMENTS 5,792,135 A 8/1998 Madhani et al.
5,817,084 A 10/1998 Jensen
(Continued)

FOREIGN PATENT DOCUMENTS

EP 2 168 512 A1 3/2010
EP 3 225 202 A1 10/2017

OTHER PUBLICATIONS

U.S. Appl. No. 15/637,683, filed Jun. 29, 2017.
(Continued)

*Primary Examiner* — Melanie R Tyson
(74) *Attorney, Agent, or Firm* — Frost Brown Todd LLC

(57) ABSTRACT

A surgical access device includes a cannula and a housing assembly coupled to a proximal end of the cannula. A working channel defined by a cannula lumen and a housing interior extends between proximal and distal ends of the surgical access device along a central axis thereof. The working channel is configured to receive a surgical instrument, and an insufflation port is configured to direct insufflation fluid into the working channel. First and second needle ports open to the working channel through respective first and second side portions of the surgical access device. The first needle port is diametrically opposed from the insufflation port. Each of the first and second needle ports is configured to direct a suture passer needle through the surgical access device, across the working channel, at an oblique angle relative to the central axis.

20 Claims, 12 Drawing Sheets

(51) Int. Cl.
   *A61B 17/06* (2006.01)
   *A61B 17/00* (2006.01)
(52) U.S. Cl.
   CPC .......... *A61B 2017/00637* (2013.01); *A61B 2017/00663* (2013.01); *A61B 2017/06042* (2013.01); *A61B 2017/346* (2013.01); *A61B 2017/3419* (2013.01); *A61B 2017/3445* (2013.01)
(58) Field of Classification Search
   CPC .... A61B 2017/3449; A61B 2017/3466; A61B 2017/3419
   See application file for complete search history.

(56) References Cited

U.S. PATENT DOCUMENTS

| | | | |
|---|---|---|---|
| 5,878,193 A | 3/1999 | Wang et al. |
| 6,231,565 B1 | 5/2001 | Tovey et al. |
| 6,364,888 B1 | 4/2002 | Niemeyer et al. |
| 6,783,524 B2 | 8/2004 | Anderson et al. |
| 7,524,320 B2 | 4/2009 | Tierney |
| 7,691,098 B2 | 4/2010 | Wallace et al. |
| 7,806,891 B2 | 10/2010 | Nowlin et al. |
| 7,981,092 B2 | 7/2011 | Duke |
| 8,226,553 B2 | 7/2012 | Shelton, IV et al. |
| 8,251,900 B2 | 8/2012 | Ortiz et al. |
| 8,479,969 B2 | 7/2013 | Shelton, IV |
| 8,568,362 B2 | 10/2013 | Moreno et al. |
| 8,573,461 B2 | 11/2013 | Shelton, IV et al. |
| 8,573,465 B2 | 11/2013 | Shelton, IV |
| 8,579,807 B2 | 11/2013 | Moreno et al. |
| 8,602,288 B2 | 12/2013 | Shelton, IV et al. |
| 8,616,431 B2 | 12/2013 | Timm et al. |
| 8,636,686 B2 | 1/2014 | Minnelli et al. |
| 8,690,831 B2 | 4/2014 | Duke |
| 8,783,541 B2 | 7/2014 | Shelton, IV et al. |
| 8,800,838 B2 | 8/2014 | Shelton, IV |
| 8,820,605 B2 | 9/2014 | Shelton, IV |
| 8,844,789 B2 | 9/2014 | Shelton, IV et al. |
| 8,979,747 B2 | 3/2015 | Auerbach et al. |
| 9,301,759 B2 | 4/2016 | Spivey et al. |
| 9,687,226 B2 | 6/2017 | Hodgkinson et al. |
| 9,700,303 B2 | 7/2017 | Prior et al. |
| 2008/0200950 A1 | 8/2008 | Wohlert |
| 2015/0038793 A1 | 2/2015 | Prior et al. |
| 2017/0079639 A1* | 3/2017 | Mohajer-Shojaee ............... A61B 17/0482 |
| 2017/0281154 A1 | 10/2017 | Hess et al. |

OTHER PUBLICATIONS

U.S. Appl. No. 15/637,690, filed Jun. 29 2017.
U.S. Appl. No. 15/637,696, filed Jun. 29, 2017.
U.S. Appl. No. 15/637,702, filed Jun. 29 2017.
U.S. Appl. No. 15/637,707, filed Jun. 29, 2017.
U.S. Appl. No. 15/637,712, filed Jun. 29, 2017.
U.S. Appl. No. 15/637,735, filed Jun. 29, 2017.
U.S. Appl. No. 15/637,778, filed Jun. 29, 2017.
European Search Report and Written Opinion dated Oct. 9, 2018 for Application No. EP 18180459.2, 8 pgs.
International Search Report and Written Opinion dated Oct. 9, 2018 for Application No. PCT/IB2018/054524, 12 pgs.

* cited by examiner

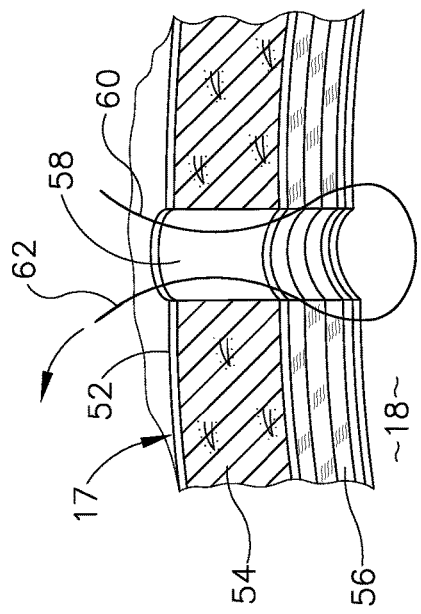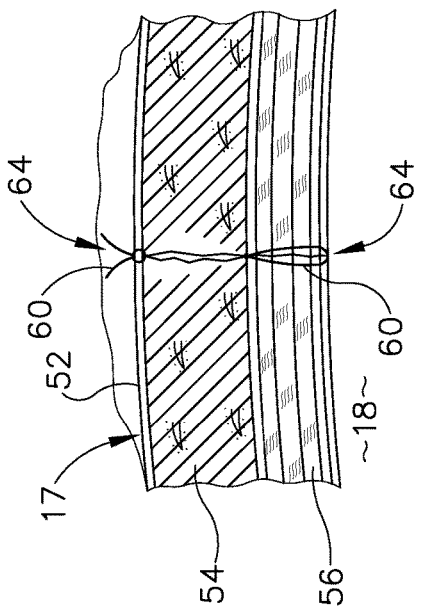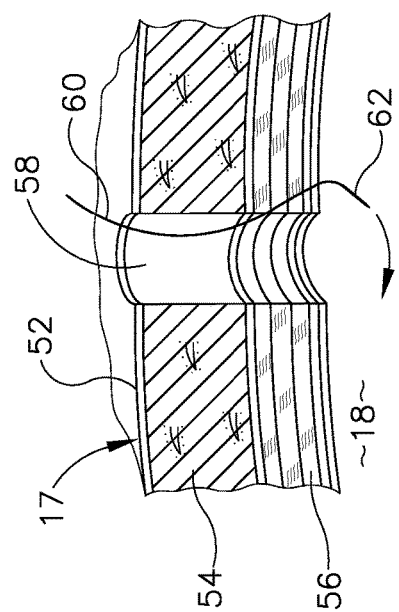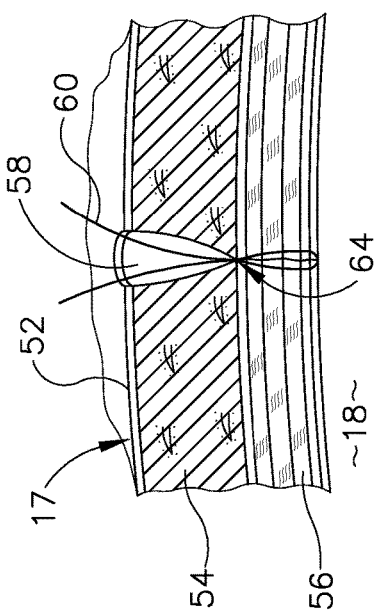

TROCAR WITH OBLIQUE NEEDLE INSERTION PORT AND COPLANAR STOPCOCK

BACKGROUND

Surgical procedures may require a clinician to gain access to a cavity or other desirable surgical site within a body of a patient. To perform such a surgical procedure, an incision may be made through a tissue of the patient into the cavity. Some conventional surgical procedures may apply a knife, such as a scalpel, to the tissue for the incision, while some less invasive surgical procedures, such as laparoscopic and endoscopic surgical procedures, may access the cavity through a trocar assembly. Traditional trocar assemblies generally include a trocar obturator received within a trocar cannula. In use, the clinician directs the trocar obturator and the cannula through the tissue in order to access the cavity of the desirable surgical site. Once accessed, the clinician withdraws the trocar obturator from the trocar cannula so that the trocar cannula may be used to introduce surgical instruments into the cavity for treatment.

Examples of trocar assemblies, components thereof, and other varieties of surgical access devices and wound closure devices are provided for in U.S. Pat. No. 7,981,092, entitled "Vibratory Trocar," issued Jul. 19, 2011; U.S. Pat. No. 8,226,553, entitled "Access Device with Insert," issued on Jul. 24, 2012; U.S. Pat. No. 8,251,900, entitled "Surgical Access Devices and Methods Providing Seal Movement in Predefined Paths," issued on Aug. 28, 2012; U.S. Pat. No. 8,579,807, entitled "Absorbing Fluids in a Surgical Access Device," issued on Nov. 12, 2013; U.S. Pat. No. 8,568,362, entitled "Surgical Access Device with Sorbents," issued on Oct. 29, 2013; U.S. Pat. No. 8,636,686, entitled "Surgical Access Device," issued on Jan. 28, 2014; U.S. Pat. No. 8,690,831, entitled "Gas Jet Fluid Removal in a Trocar," issued on Apr. 8, 2014; U.S. Pat. Pub. No. 2008/0200950, entitled "Surgical Hook," published on Aug. 21, 2008; U.S. Pat. Pub. No. 2015/0038793, entitled "Devices, Systems, and Methods for Providing Surgical Access and Facilitating Closure of Surgical Access Openings," published on Feb. 5, 2015; U.S. Pat Pub. No. 2015/0038994, entitled "Devices, Systems, and Methods for Providing Surgical Access and Facilitating Closure of Surgical Access Openings," published on Feb. 5, 2015; and U.S. Pat. Pub. No. 2015/0094741, entitled "Wound Closure Device including Mesh Barrier." Published on Apr. 2, 2015. The disclosure of each of the above-cited U.S. Patents and Publications is incorporated by reference herein.

Surgical instruments for use with such surgical access devices may have a distal end effector for engaging tissue through the access device in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Laparoscopic and endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the cavity of the patient. Positioning of an end effector may be further facilitated through inclusion of one or more articulation joints or features, enabling the end effector to be selectively articulated or otherwise deflected relative to the longitudinal axis of the shaft.

While various kinds of surgical instruments, including surgical access devices and end effectors, and other associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 4A depicts another side sectional view of the tissue shown in FIGS. 3A-3D following removal of the trocar assembly of FIG. 1, with an opening through the tissue and a suture thread being introduced into a portion of the tissue for suturing the opening closed;

FIG. 4B depicts a side sectional view of the tissue of FIG. 4A, with the suture thread being introduced though another portion of the tissue and pulled through the tissue;

FIG. 4C depicts a s side sectional view of the tissue of FIG. 4A, with the suture thread tightened and knotted for at least partially closing the opening;

FIG. 4D depicts a side sectional view of the tissue of FIG. 4A, with additional suturing for further closing the opening;

Figure 1:
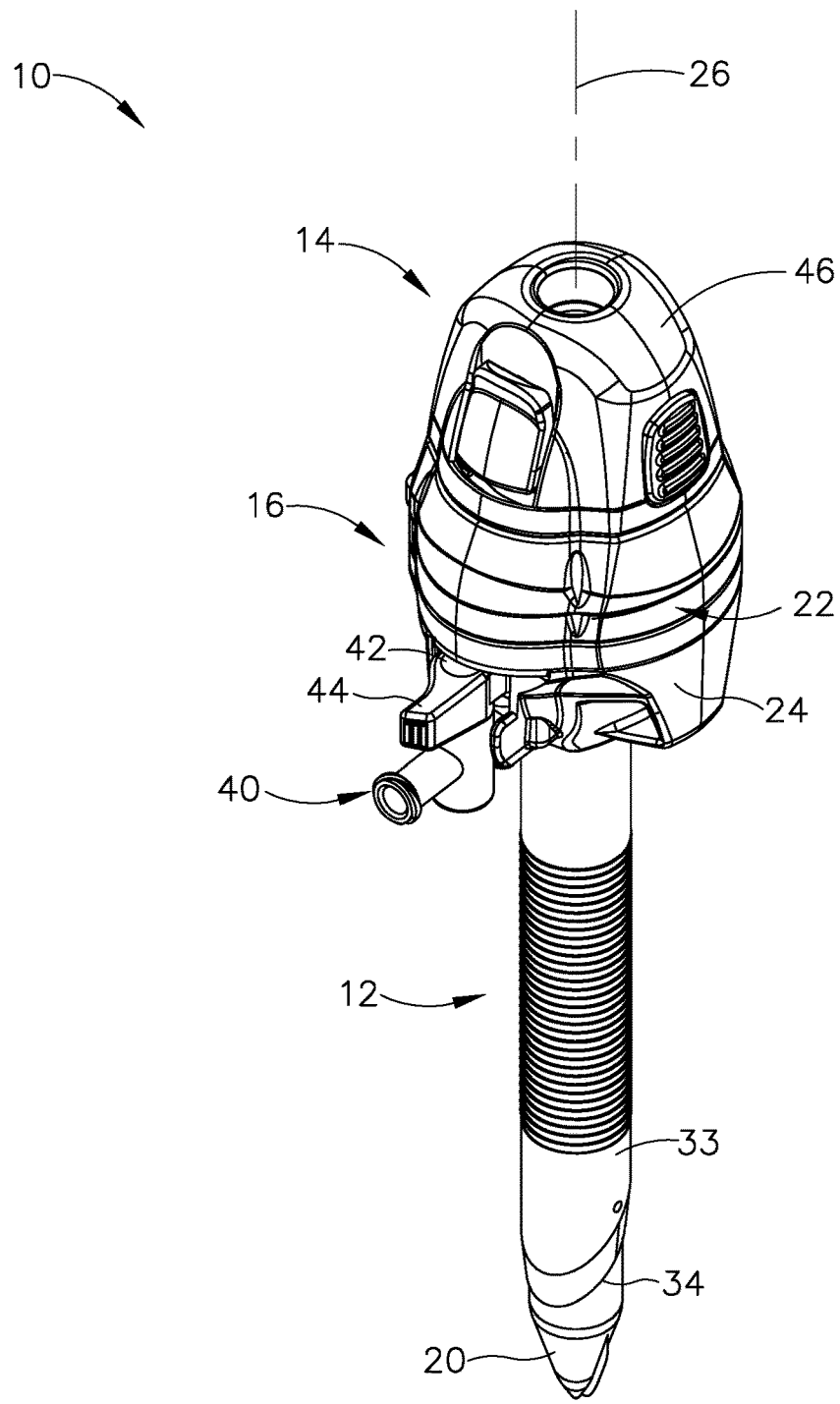
FIG. 1 depicts a perspective view of an exemplary trocar assembly.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Access Device

Figure 2:
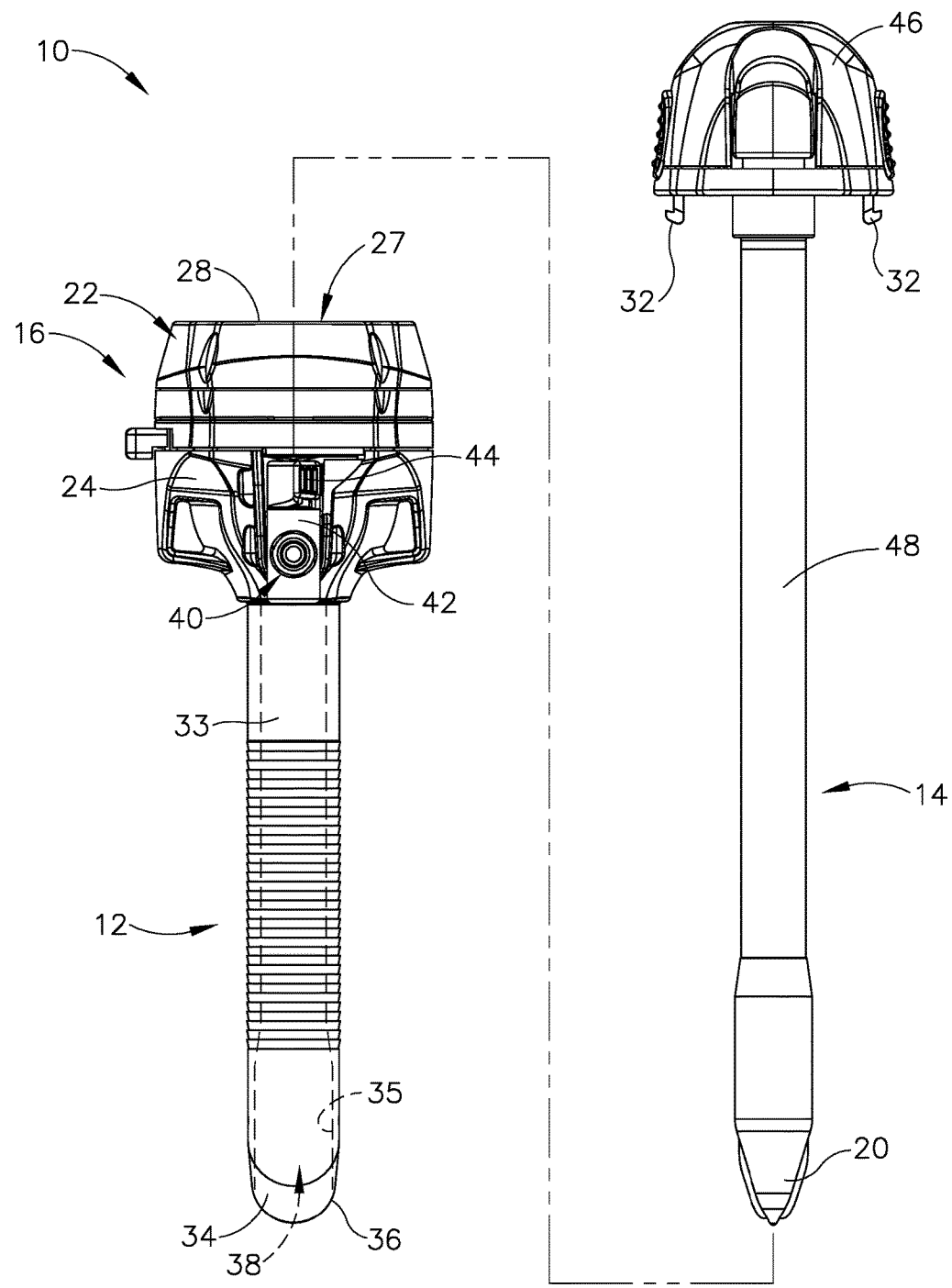
FIG. 2 depicts a partially exploded side elevational view of the trocar assembly of FIG. 1 having a trocar housing, a trocar cannula, and an obturator.

FIGS. 1-2 depict an exemplary surgical access device in the form of a first exemplary trocar assembly (10) that includes a trocar cannula (12) and a trocar obturator (14). Trocar obturator (14) is removably received within trocar cannula (12) through a trocar housing (16) of trocar cannula (12). As shown in FIG. 1 with trocar obturator (14) positioned within trocar cannula (12), a clinician inserts trocar assembly (12) through tissue (17) (see FIG. 3A) of a patient at a desirable surgical site for accessing a cavity (18) (see FIG. 3A) within the patient. By way of example only, trocar assembly (10) may be inserted in a patient's abdomen, between two of the patient's ribs, or elsewhere. A tip (20) of trocar obturator (14) projects distally from trocar cannula (12) to puncture tissue (17) (see FIG. 3A) for introducing a distal end portion of trocar cannula (12) into cavity (18) (see FIG. 3B). The clinician proximally withdraws trocar obturator (14) from trocar cannula (12) such that cavity (18) (see FIG. 3C) within the patient is in communication with a surgical environment via trocar cannula (12). The clinician may then introduce a fluid, such as a gas, through trocar cannula (12) for inflating cavity (18) (see FIG. 3A) and/or an end effector of a surgical instrument through trocar cannula (12) for engaging tissue (17) to achieve a diagnostic or therapeutic effect.

It should be understood that terms such as "proximal" and "distal" are used herein with reference to the clinician gripping trocar housing (16). Thus, tip (20) is distal with respect to the more proximal trocar housing (16). It will be further appreciated that for convenience and clarity, spatial terms such as "vertical" and "horizontal" are used herein with respect to the drawings. However, surgical instruments are used in many orientations and positions, and these terms are not intended to be limiting and absolute. Further, in some instances, components are referred to interchangeably with and without the term "assembly," e.g., a trocar and a trocar assembly. There is no particular intention for the terms to refer to different components. Likewise, terms such as "instrument" and "device" may be used interchangeably.

A. Exemplary Trocar Assembly with Cannula and Obturator

Trocar assembly (10) of FIGS. 1-2 includes cannula (12) extending distally from trocar housing (16). In the present example, trocar housing (16) has a generally cylindrical shape with a proximal removable cap (22) atop a distal housing chamber (not shown). Cap (22) is selectively attachable and detachable from housing chamber (not shown). Trocar housing (16) includes a housing sidewall (24) that extends circumferentially around a central longitudinal axis (26) through trocar assembly (10), and thus along trocar cannula (12). Trocar housing (16) further includes a central lumen (27) extending from a proximal housing end opening (28) to a distal housing end opening (not shown). As shown, cap (22) selectively mates with housing sidewall (24) via distal mating members (not shown) and further includes proximal mating members, such as slots (not shown), configured to removably connect to a pair of tabs (32), respectively, that extend distally from a portion of obturator (14). However, it will be appreciated that alternative structures and devices may also be removably connected to cap (22) during use.

Cannula (12) extends distally from trocar housing (16), and is also generally defined by a cannula sidewall (33) extending circumferentially around central longitudinal axis (26). Cannula sidewall (33) extends distally to a beveled end (34) such that cannula sidewall (33) and beveled end (34) are configured to be inserted through tissue (17) (see FIG. 3A) as discussed below in greater detail for accessing cavity (18) (see FIG. 3A). To this end, cannula (12) generally has a smaller diameter than trocar housing (16), which is configured to remain exterior of tissue (17) (see FIG. 3C). In addition, cannula (12) defines an interior lumen (35) with a proximal cannula end opening (not shown) and a distal cannula end opening (36), which extends through beveled end (34). In the present example, distal housing end opening (not shown) of trocar housing (16) fluidly connects to proximal cannula end opening (not shown) such that central lumen (27) of trocar housing (16) and interior lumen (35) of cannula (12) define a working channel (38). Working channel (38) thus extends from proximal housing end opening (28) to distal cannula end opening (36) and is configured to receive one or more surgical instruments therethrough for accessing cavity (18).

Furthermore, an insufflation port (40) is operatively connected to trocar housing (16) to control the flow of an insufflation fluid, such as carbon dioxide, through a portion of cannula (12) and into cavity (18). More particularly, insufflation port (40) includes a stopcock valve (42) and a cock valve lever (44), which can work together to allow and/or prevent passage of the insufflation fluid into tubing (not shown), through trocar housing (16), and into trocar cannula (12). Trocar housing (16) and cannula (12) respectively have proximal and distal seal assemblies (not shown) positioned within central lumen (27) and interior lumen (35) of working channel (38). In the present example, the proximal seal assembly is an instrument seal (not shown), whereas the distal seal assembly (not shown) is a zero-closure seal, such as a duckbill seal (not shown). Instrument seal (not shown) is retained within cap (22) and is configured to fluidly seal against a surgical instrument extending through working channel (38). In contrast, duckbill seal (not shown) is configured to form a seal in working channel (38) when no instrument is disposed therethrough to thereby inhibit the leakage of insufflation fluid during use. Of course, it will be appreciated that alternative seal assemblies may be positioned within working channel (38) for inhibiting such leakage of insufflation fluid.

Duckbill seal is further configured to be manipulated to provide an opening to working channel (38) that is larger than a corresponding opening provided by instrument seal. This larger opening provided by duckbill seal may facilitate extraction of bodily tissue through trocar housing (16)

during a surgical procedure. In particular, cap (22) may be removed, and proximal instrument seal along with it, to expose the duckbill seal and thereby enable a surgeon to extract bodily tissue proximally through the duckbill seal opening that would otherwise be too large to extract proximally through the instrument seal opening.

As discussed briefly above, obturator (14) is used in conjunction with cannula (12) for inserting trocar assembly (10) into the patient. Obturator (14) of the present example, includes a handle head (46) with a cylindrical shaft (48) extending distally therefrom to tip (20), which is generally configured to puncture tissue (17) (see FIG. 3A) as described below in greater detail. Handle head (46) is configured to be gripped by the clinician during use and includes selectively movable tabs (32) extending distally to removably connect with trocar housing (16) for selective securement. Shaft (48) is received through working channel (38) such that tip (20) extends distally from beveled end (34). Of course, obturator (14) may be selectively removed from cannula (12) and trocar housing (16) to free working channel (38) for use. While the present example of trocar assembly (10) has obturator (14), it will be appreciated that cannula (12) may be inserted in some examples without obturator (14) or may be alternatively configured to aid insertion without using obturator (14).

B. Exemplary Method of Accessing a Cavity within a Patient

Figure 3A:
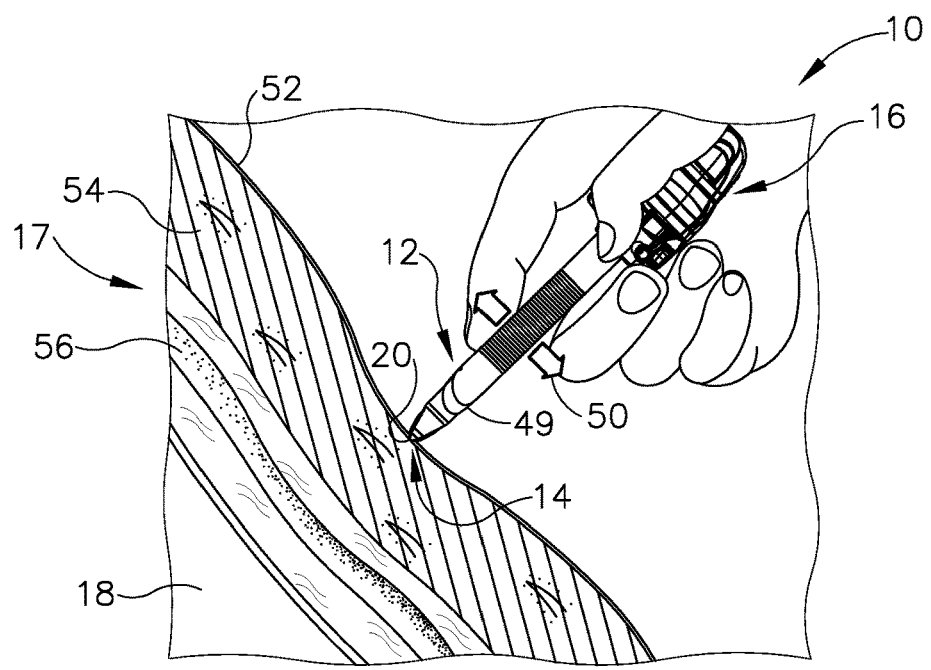
FIG. 3A depicts a side sectional view of tissue of a patient with the trocar assembly of FIG. 1 being manipulated by a clinician through the tissue.
Figure 3B:
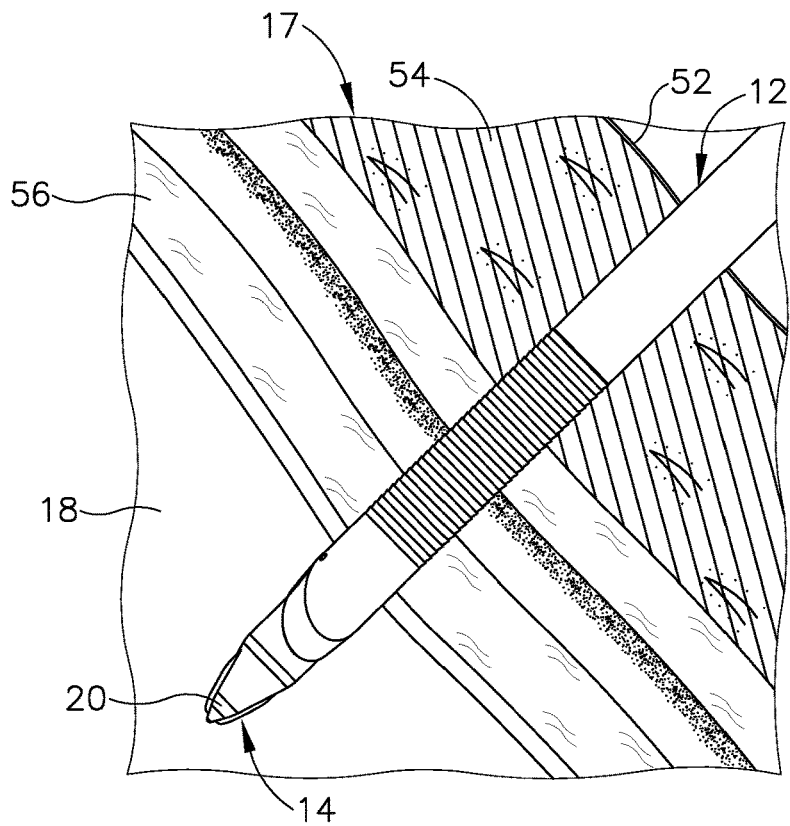
FIG. 3B depicts a side sectional view of the tissue and trocar assembly of FIG. 3A, with the trocar assembly of FIG. 1 inserted through the tissue and received within a cavity of the patient.
Figure 3C:
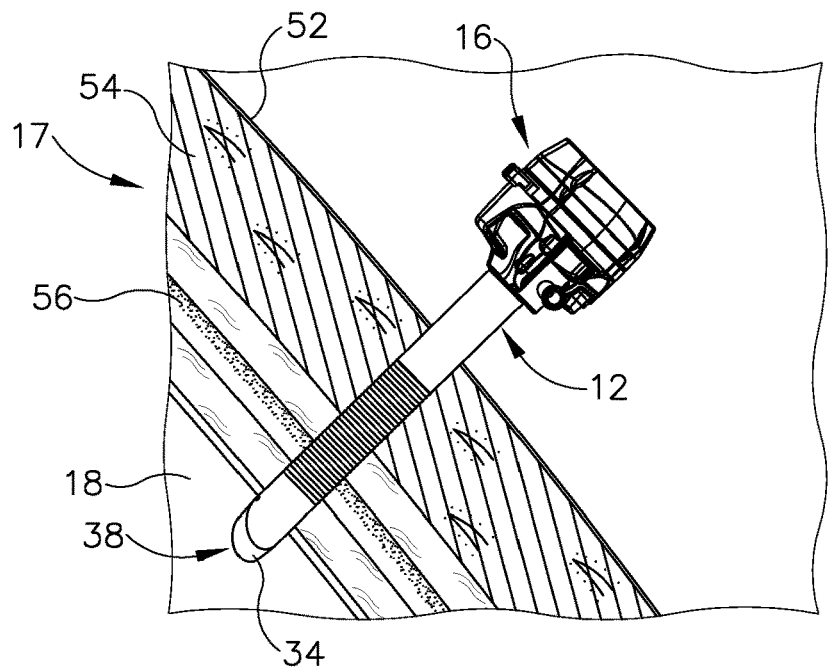
FIG. 3C depicts a side sectional view of the tissue and the trocar assembly of FIG. 3A, with the obturator withdrawn from the trocar cannula for accessing the cavity via a working channel through the trocar cannula and the trocar housing.
Figure 3D:
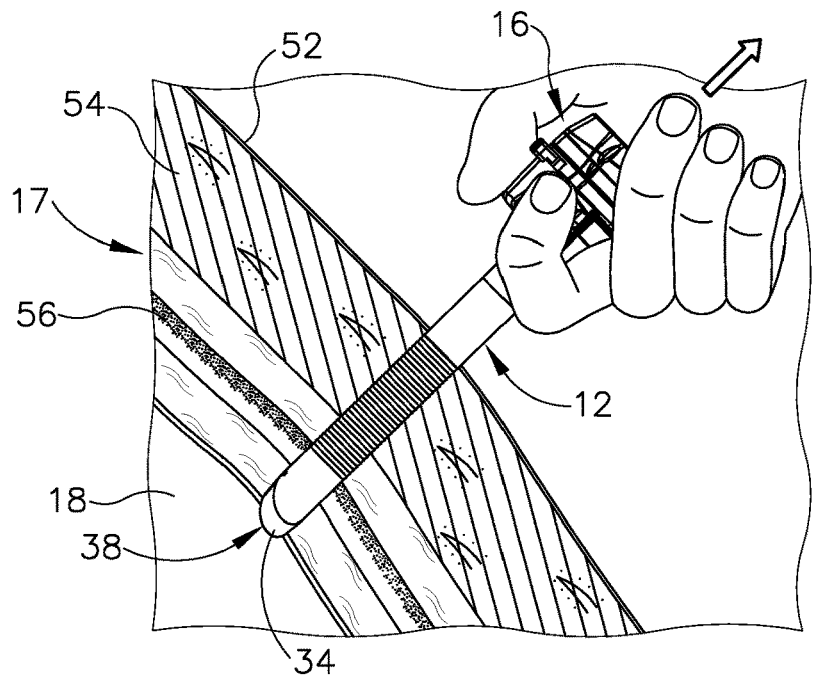
FIG. 3D depicts a side sectional view of the tissue and the trocar assembly of FIG. 3C, with the trocar housing and the trocar cannula being removed from the cavity and the tissue of the patient.

FIGS. 3A-3D illustrate accessing cavity (18) through tissue (17) with trocar assembly (10) discussed above. Tissue (17) of the present example more particularly has relatively outward superficial layers and relatively inward deep layers. Superficial layers generally include an outer layer of skin (52) and an inner layer of fat (54); whereas the deeper layers include layers of fascia (56), which are fibrous and flexible with relatively higher tensile strength than the superficial layers. As shown in FIG. 3A, with obturator (14) received within cannula (12) and connected to trocar housing (16), the clinician manipulates trocar assembly (10) to urge tip (20) of obturator (14) against skin (52) and inward toward cavity (18) while rotating trocar assembly (10) back and forth. Arrow (49) and arrow (50) respectively indicate this inward and rotatable movement. Continued inward urging of trocar assembly (10) further directs tip (20) and beveled end (34) of cannula (12) through the layers of fat (54) and fascia (56) and into cavity (18) as shown in FIG. 3B. The clinician then disconnects obturator (14) from trocar housing (16) and withdraws obturator (14) from cannula (12) to establish access from the exterior of tissue (17) into cavity (18) via working channel (38) as shown in FIG. 3C for achieving a diagnostic or therapeutic effect with another surgical instrument (not shown). Once the diagnostic or therapeutic effect is complete, clinician withdraws cannula (12) and trocar housing (16) outwardly for removal from tissue (17) as shown in FIG. 3D.

As shown in FIG. 4A, removal of cannula (12) from tissue (17) generally results in a tissue opening (58), which may also be referred to as a tissue port or tissue wound, that clinician closes to encourage healing of tissue (17). While some tissue openings may sufficiently close as tissue (17) comes together, other openings, such as tissue opening (58), are sutured closed with a suture thread (60). In one example shown in FIGS. 4A-4D, suture thread (60) is removably coupled with a needle (62) for guiding suture thread (62) through tissue (17) as the clinician manipulates needle (62). More particularly, as shown in FIG. 4B, the clinician directs needle (62) downwardly through fascia (56) on one side of tissue opening (58) and then upwardly through fascia (56) on the other side of tissue opening (58) as needle (62) clears tissue (17). Notably, the clinician threads needle (62) though fascia (56) a desirable distance distally from tissue opening (58) in order to provide a relatively close proximity to tissue opening (58); but also at a sufficient distance to provide ample fascia (56) for anchoring suture thread (60) therein. Additionally, the clinician angles a tip of needle (62) obliquely away from a central axis of opening (58) at a suitable angle in order to achieve sufficient "bite" when anchoring suture thread (60) within fascia (56). As shown in FIG. 4C, suture thread (60) from respective sides of tissue opening (58) are brought together and pulled to similarly pull tissue (17) together and at least partially close tissue opening (58). The clinician then knots suture thread (60) to secure tissue (17) together and sufficiently close tissue opening (58) with a formed suture (64) as shown in FIG. 4D. Additional sutures (64) may be placed along tissue (17) to further close tissue opening (58) and encourage healing of tissue (17).

While the above described suturing technique shown in FIGS. 4A-4D is one exemplary procedure for closing tissue opening (58) with suture thread (60) following use of trocar assembly (10) (see FIG. 1), other exemplary procedures and devices may be alternatively used for closing such tissue openings. By way of example, U.S. patent application Ser. No. 15/088,723, entitled "Surgical Access Devices with Integrated Wound Closure Features," filed Apr. 1, 2016, which is incorporated by reference herein in its entirety, describes an alternative trocar assembly and suturing technique. To this end, alternative trocar assemblies and suturing techniques may be used in any combination as desired by the clinician.

II. Exemplary Surgical Access Devices Having Wound Closure Features

A. Exemplary Trocar Having Needle Ports and Insufflation Port in First Arrangement FIGS. 5-8 show another exemplary surgical access device in the form of a trocar (100). Though not shown, those of ordinary skill in the art will recognize that trocar (100) may be used in combination with any suitable trocar obturator, such as obturator (14) described above, for example. Trocar (100) generally includes a housing assembly (102) and a cannula (104) coupled to and extending distally from housing assembly (102) along a central longitudinal axis of trocar (100). Housing assembly (102) includes a proximal housing (106), a housing cap plate (108), a latch ring (110), and a distal housing (112). Proximal housing (106) has a proximal housing head (114) and a proximal housing base (116). Proximal housing (106) is coupled with and selectively releasable from the remainder of trocar (100) via housing cap plate (108) and latch ring (110). As described in greater detail below, trocar (100) further includes a plurality of needle entrance ports (150) and needle exit ports (152) defining a corresponding plurality of suture paths extending obliquely through trocar (100) across its central axis. In the present example, at least one of the needle entrance ports (150), and a corresponding needle guide structure (154), is positioned in diametric opposition to an insufflation port (134) of trocar (100), in a coplanar relationship.

Figure 6:
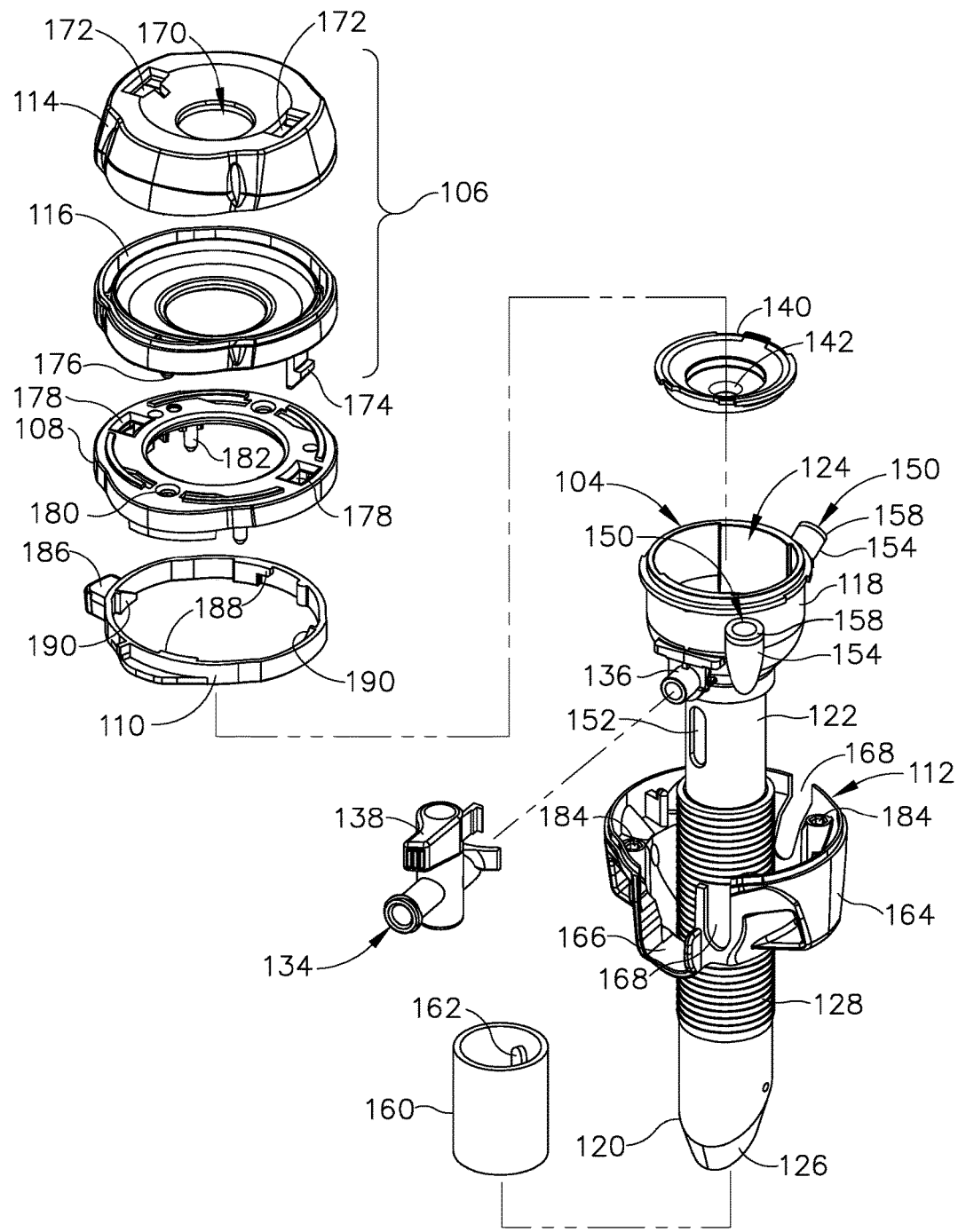
FIG. 6 depicts an exploded perspective view of the trocar of FIG. 5.

As shown in FIG. 6, cannula (104) includes a proximal hub (118), a distal tip (120), and a cylindrical body (122) extending therebetween along the central axis of trocar (100). Proximal hub (118) flares radially outwardly from cylindrical body (122) in a proximal direction and defines a proximal opening to a cannula lumen (124), while distal tip (120) defines a distal opening to cannula lumen (124). Distal tip (120) itself is beveled and includes a chamfered edge (126) configured to facilitate insertion of distal tip (120) through tissue and into a patient body cavity during a surgical procedure. An outer surface of cylindrical body (122) may be provided with a plurality of tissue engagement ribs (128) or other similar features suitable to frictionally engage the inner wall of a tissue opening through which cannula (104) is received into the body cavity.

Figure 7:
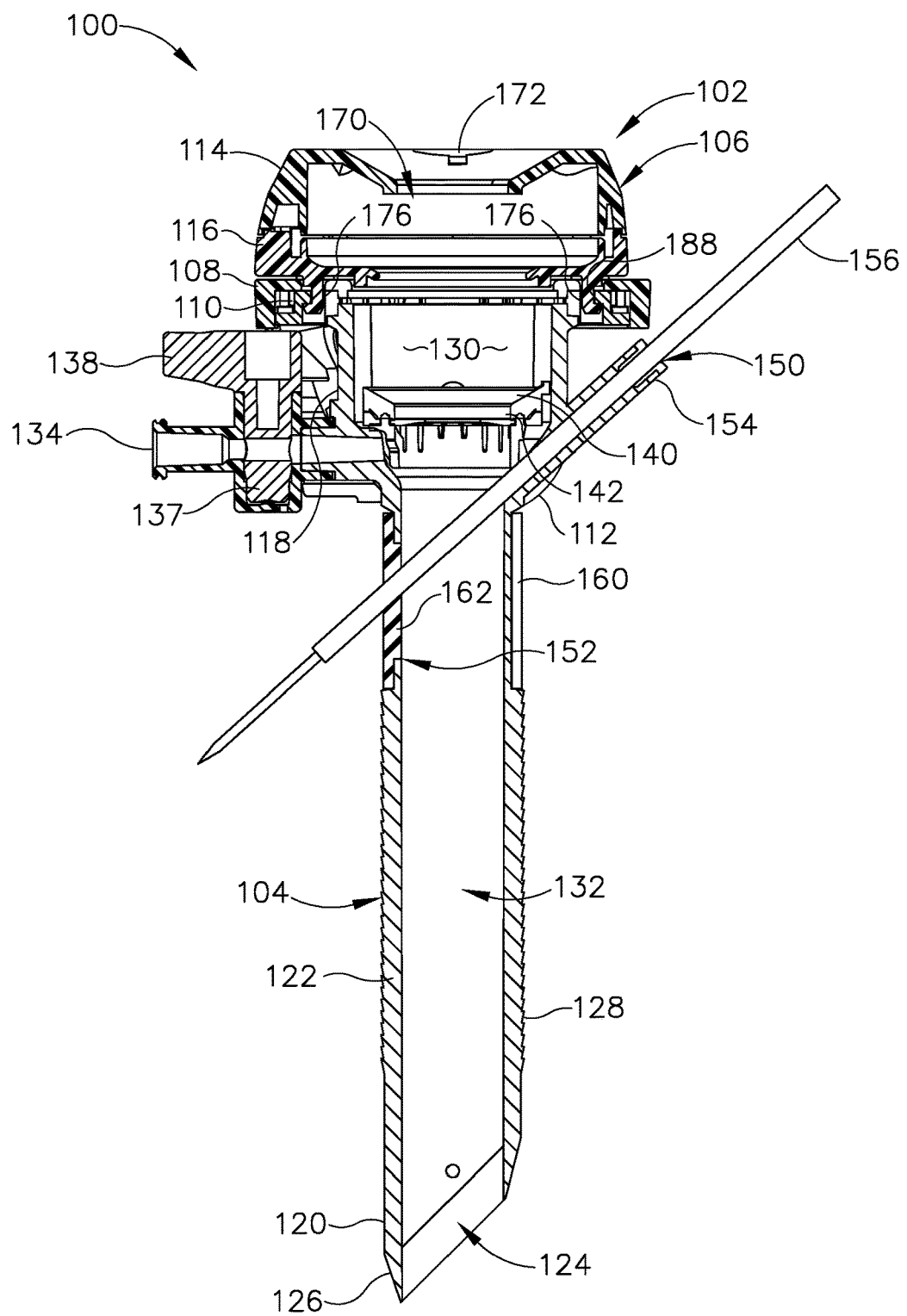
FIG. 7 depicts a side sectional view of the trocar of FIG. 5, showing an exemplary suture needle passer extending through the trocar along an exemplary first suture path oriented obliquely relative to a central axis of the trocar.

As shown in FIG. 7, cannula lumen (124) fluidly communicates with an interior (130) of housing assembly (102) to collectively define a working channel (132) extending through trocar (100) along the central axis thereof. A distal opening to working channel (132) is defined by distal tip (120) of cannula (104), and a proximal opening to working channel (132) is defined by proximal housing head (114). When proximal housing (106) is decoupled from the remainder of trocar (100), the proximal opening to working channel (132) is defined by housing cap plate (108). Working channel (132) is configured to receive one or more surgical instruments therethrough, such as a variety of endoscopic surgical instruments, for example, for accessing the patient body cavity and observing and/or treating tissue accessible therein.

As shown in FIGS. 6 and 7, an insufflation port (134) (or "stopcock") is operatively connected to proximal hub (118) of cannula (104) at fitting (136). Insufflation port (134) includes an internal valve (137) and a valve lever (138), and may be formed integrally with fitting (136), or alternatively coupled to fitting (136) during assembly of trocar (100). Insufflation tubing (not shown) is coupled to an inlet of insufflation port (134) and directs insufflation fluid, such as carbon monoxide, from a fluid source into insufflation port (134), which directs the fluid distally through working channel (132) into the patient body cavity. Valve lever (138) is configured to rotate the internal valve (137) between open and closed positions to control the flow of insufflation fluid through insufflation port (134).

Similar to trocar assembly (10), trocar (100) may include a proximal (or "outer") seal assembly and/or a distal (or "inner") seal assembly, each arranged within working channel (132). In the present example, trocar (100) includes a distal seal assembly in the form of an instrument seal (140) arranged within a tapered portion of proximal hub (118). Distal instrument seal (140) includes a central opening (142) configured to receive a surgical instrument therethrough, and is configured to sealingly engage an outer surface of the surgical instrument to prevent proximal advancement of bodily fluids and/or tissue into housing assembly interior (130). In exemplary configurations, instrument seal (140) may be configured to absorb or otherwise remove bodily fluids from the outer surface of the surgical instrument as the surgical instrument is retracted proximally through instrument seal (140).

Those of ordinary skill in the art will recognize that trocar (100) may include proximal and/or distal seal assemblies of various suitable configurations, such as those disclosed in U.S. patent application Ser. No. 15/088,723, incorporated by reference above. For instance, though not shown, trocar (100) may include a proximal seal assembly in the form of an instrument seal arranged within proximal housing (106), and/or a distal seal assembly in the form of a zero-closure seal, such as a duckbill seal, arranged within proximal hub (118) of cannula (104). As described above with reference to trocar assembly (10), such a zero-closure seal is generally configured to form a fluid-tight seal in working channel (132) and thereby maintain insufflation even when no surgical instrument is present in working channel (132). Furthermore, the distal zero-closure seal may be manipulated to provide an opening to a distal portion of working channel (132) (e.g., cannula lumen (124)) that is large enough to enable extraction of tissue proximally therethrough, particularly when proximal housing (106) is separated from trocar (100) to provide access to the distal zero-closure seal.

As shown in FIG. 6, trocar (100) further includes a plurality of needle ports formed in select side portions of cannula (104). As described in greater detail below, each needle port is configured to direct a suture passer needle (or simply "suture passer") across working channel (132) of trocar (100) at an oblique angle relative to the central axis of trocar (100) to thereby establish an oblique suture path extending through trocar (100) and adjacent tissue. As used herein, the term "oblique" means neither parallel nor perpendicular to the referenced axis, such as the central axis of trocar (100).

Figure 5:
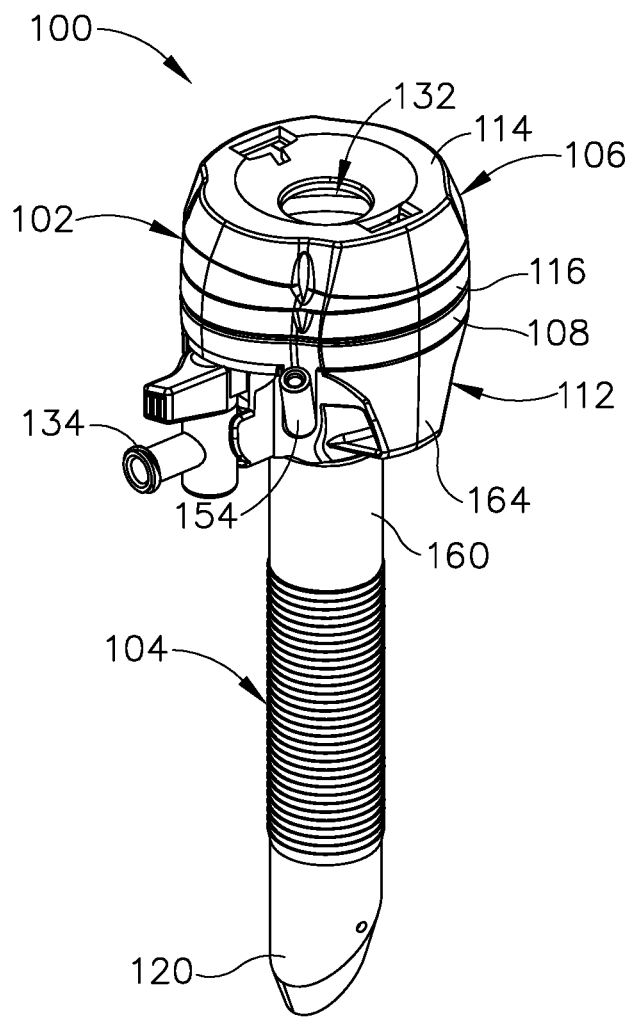
FIG. 5 depicts a perspective view of an exemplary trocar having a housing assembly, cannula, and needle ports.

In the present example, trocar (100) includes a pair of needle entrance ports (150) and a corresponding pair of needle exit ports (152) arranged distally of needle entrance ports (150). Each needle entrance port (150) is defined by a respective needle guide structure shown in the form of a needle guide tube (154) formed integrally with and projecting obliquely outwardly from proximal hub (118) at a respective side portion of cannula (104). Needle entrance ports (150) extend through proximal hub (118) and open to cannula lumen (124), as best shown in FIG. 7. As best shown in FIGS. 5-7, each needle exit port (152) extends through cylindrical body (122) of cannula (104) and opens to cannula lumen (124) at a position generally diametrically opposed from a respective one of needle entrance ports (150) and its corresponding needle guide tube (154). In the present example, each needle exit port (152) is generally elongate along the central axis of trocar (100), though needle exit ports (152) may be formed with various other shapes in alternative examples.

As used herein with reference to various first and second structures or reference points, the term "diametrically opposed" encompasses but is not limiting to a configuration in which the referenced structures or reference points are located at the same longitudinal position along the central axis of trocar (100). For instance, in the present example each needle entrance port (150) is spaced proximally from its respective needle exit port (152), though ports (150, 152) are still understood to be diametrically opposed from one another along the same axially extending plane containing the central axis of trocar (100). Of course, in alternative versions of trocar (100), a needle entrance port (150) may lie in a first plane containing the trocar central axis while the corresponding needle exit port (152) lies in a second plane containing the central trocar axis and being offset from the first plane, such that the needle entrance and exit ports (150, 152) are not diametrically opposed from one another.

As best shown in FIG. 7, each needle entrance port (150) and its respective needle guide tube (154) is configured to cooperate with an opposing needle exit port (152) to direct a suture passer needle (156) along a respective suture path that extends obliquely relative to the central axis of trocar (100). In particular, a needle entrance port (150) and its respective needle guide tube (154) on a first side portion of cannula (104) cooperate with a needle exit port (152) on a second side portion of cannula (104) to define a first oblique suture path. Additionally, a needle entrance port (152) and its respective needle guide tube (154) on the second side portion of cannula (104) cooperate with a needle exit port (152) on the first side portion of cannula (104) to define a second oblique suture path.

Each needle exit port (152) is spaced distally from its respective needle entrance port (150) by a distance suitable to achieve a desired suture path angle (or "tissue bite angle") measured between the resulting suture path and the central axis of trocar (100). In the present example, each needle exit port (152) is spaced distally from its respective needle entrance port (150) by the same axial distance, such that the resulting suture paths exhibit the same suture path angles. In other examples, however, needle exit ports (152) may be spaced distally from their respective needle entrance ports (150) by different axial distances to achieve different suture path angles.

While the needle guide structures of the present example are shown in the form of needle guide tubes (154) formed integrally with cannula (104), those of ordinary skill in the art will recognize that various other configurations and structures suitable to guide a suture passer needle (156) along the oblique suture paths of trocar (100) may be implemented. For instance, trocar (100) may be provided with needle guide tubes that are formed integrally with or otherwise defined by distal housing (112), for example as disclosed in U.S. App. No. 15/637,683, entitled "Trocar with Oblique Needle Insertion Port and Perpendicular Seal Latch," filed on even date herewith, published as U.S. Pub. No. 2019/0000505 on Jan. 3, 2019, the disclosure of which is incorporated by reference herein. In other examples, such externally-projecting needle guide structures may be omitted from trocar (100).

As shown in FIGS. 6 and 7, each needle port (150, 152) of trocar (100) is provided with a pierceable seal configured to aid in maintaining insufflation when a suture passer needle (156) is directed through trocar (100) along the suture paths, and/or when the suture passer needle (156) is withdrawn from trocar (100). In the present example, each needle entrance port (150) is provided with an entrance seal shown in the form of a seal cap (158) received within an entrance end of the respective needle guide tube (154). Further, each needle exit port (152) is provided with an exit seal shown in the form of an elongate protrusion (162) projecting radially inwardly from an inner surface of a cannula sleeve (160). As shown in FIGS. 5 and 6, cannula sleeve (160) is received over a narrowed region of cylindrical body (122) of cannula (104), and has an outer diameter similar to an outer diameter of a distal portion of cylindrical body (122) located distally of tissue engagement ribs (128). In exemplary configurations, seal caps (158) and cannula sleeve (160), including protrusions (162), may be formed of an elastomeric material. Additionally, cannula sleeve (160) and/or seal caps (158) may be formed through an overmolding process, for example.

As shown in FIGS. 5-7, distal housing (112) is in the form of a generally annular shell shaped to receive and encircle proximal hub (118) of cannula (104). Distal housing (112) includes a pair of diametrically opposed side wings (164), which may be gripped by a surgeon when introducing trocar (100) through patient tissue. Distal housing (112) further includes a cutout (166) sized and shaped to accommodate insufflation port (134) therethrough, and a pair of axially extending slots (168) sized and shaped to accommodate needle guide tubes (154) therethrough. In the present example, distal housing (112) is oriented relative to cannula (104) and needle guide tubes (154) such that slots (168) are arranged in respective sidewall portions extending between side wings (164). In alternative configurations, distal housing (112) may be oriented such that slots (168) are arranged in side wings (164) or in various other portions of distal housing (112).

Proximal housing (106), defined by proximal housing head (114) in combination with proximal housing base (116), is configured to couple with and selectively decouple from the remaining distal portion of trocar (100) via operation of latch ring (110) relative to housing cap plate (108). As shown in FIGS. 6 and 7, proximal housing head (114) includes a central opening (170) that defines a proximal end of working channel (132) of trocar (100) when proximal housing (106) is coupled with cannula (104). Proximal housing head (114) further includes a pair of slots (172) configured to receive a corresponding pair of tabs extending distally from the proximal head of an obturator, such as tabs (32) of obturator (14) shown in FIG. 2, for releasably connecting the obturator to trocar (100). Proximal housing head (114) is supported by and coupled to proximal housing base (116), for example by a snap-fit connection. Though not shown, a proximal seal assembly, such as an instrument seal, may be arranged between proximal housing head (114) and proximal housing base (116). Such a proximal seal assembly may cooperate with distal seal assembly (140), described above, to ensure a sealing engagement between trocar (100) and a surgical instrument inserted through trocar (100).

Proximal housing base (116) includes a plurality of distally extending mating features configured to facilitate attachment and release of proximal housing (106) from housing cap plate (108) and latch ring (110). In particular, as shown in FIG. 6, an underside of proximal housing base (116) includes a pair of distally extending latching tabs (174) and a pair of distally extending latching posts (176). Housing cap plate (108) includes a pair of tab slots (178) configured to receive latching tabs (174) therethrough, and a pair of post bores (180) configured to receive latching posts (176) therethrough. Housing cap plate (108) further includes a plurality of distally extending coupling posts (182) configured to be received by a corresponding plurality of coupling bores (184) formed on distal housing (112) for coupling housing cap plate (108) with distal housing (112), for example with a press-fit or snap-fit engagement.

Latch ring (110) is arranged distally of housing cap plate (108) and is housed radially inwardly of a sidewall of housing cap plate (108) at an upper proximal end of latch ring (110), and radially inwardly of distal housing (112) at a lower distal end of latch ring (110). As shown in FIG. 6, latch ring (110) includes a user engagement feature in the form of an outwardly projecting knob (186). Latch ring (110) further includes a plurality of inwardly projecting latching features in the form of a pair of latching arms (188) and a pair of cam ramps (190) spaced circumferentially between latching arms (188).

Latch ring (110) is rotatable about the central axis of trocar (100) between a latched position in which the latching features of latch ring (110) capture the distally extending features of proximal housing base (116), and an unlatched position in which the latching features of latch ring (110) release the distally extending features of proximal housing base (116) to thereby allow proximal detachment of proximal housing (106). More specifically, in the latched position, latching arms (188) engage latching posts (176), and cam ramps (190) engage latching tabs (174). In the unlatched position, latching arms (188) disengage latching posts (176), and cam ramps (190) disengage latching tabs (174), to thereby release proximal housing (106) from the remaining distal portion of trocar (100). Latch ring (110) is rotatable between the latched and unlatched positions by knob (186), which projects radially through a circumferential slot (not shown) formed in a sidewall of housing cap plate (108).

The components of housing assembly (102), including proximal housing (106), housing cap plate (108), and latch ring (110) may be further configured and operable in accordance with one or more teachings of U.S. App. No. 15/637,683, published as U.S. Pub. No. 2019/0000505 on Jan. 3, 2019, incorporated by reference above. For instance, in various examples, trocar (100) may be configured such that latch ring knob (186) remains circumferentially spaced (or "offset") from each of needle guide tubes (154) throughout a full range of permissible rotation of latch ring (110) relative to housing cap plate (108), thereby ensuring unobstructed access to needle guide tubes (154) during a suturing procedure performed with trocar (100).

Figure 8:
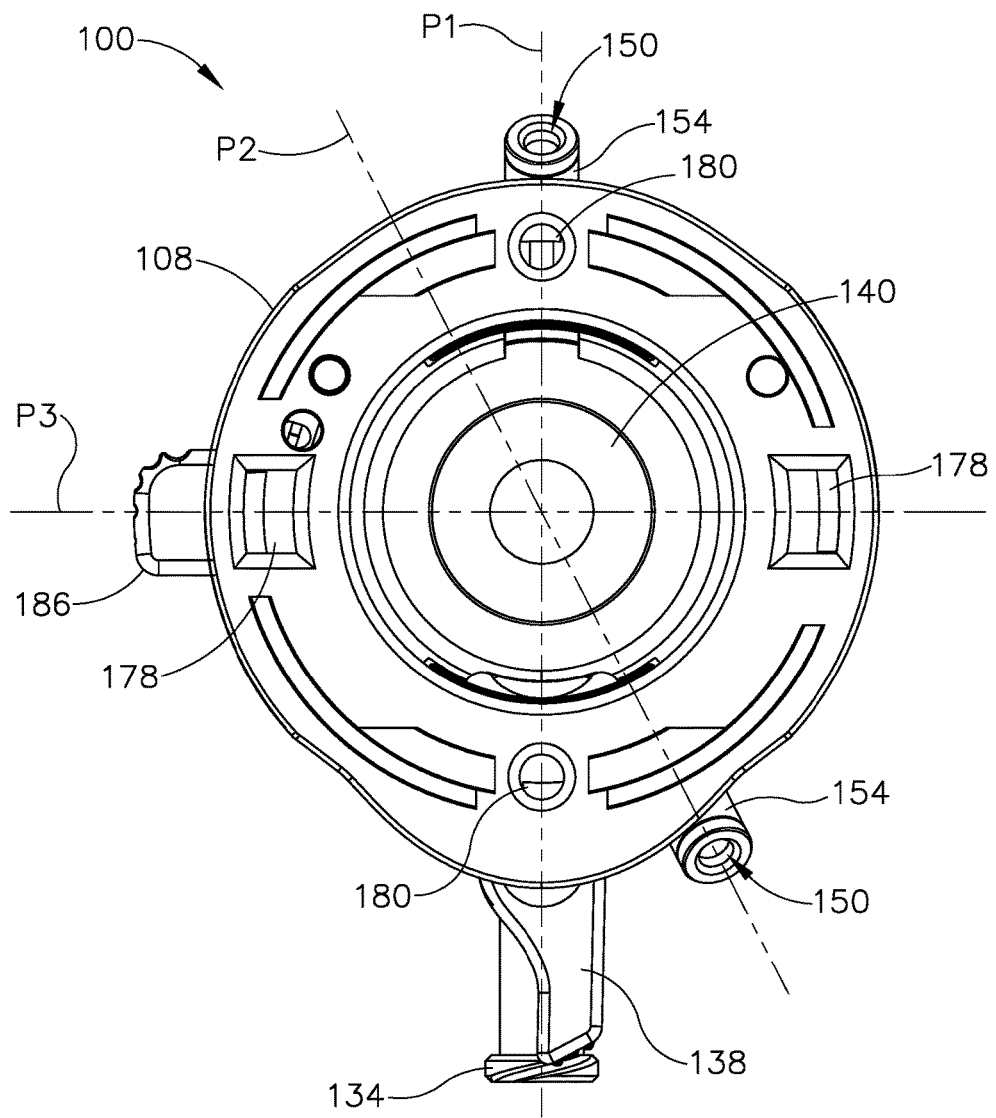
FIG. 8 depicts a top elevational view of the trocar of FIG. 5, with a proximal housing of the housing assembly being omitted.

As shown best FIG. 8, in the present example a first needle guide tube (154) and its needle entrance port (150) are arranged in diametric opposition to insufflation port (134). Accordingly, the first needle guide tube (154), its needle entrance port (150), the corresponding needle exit port (152), and insufflation port (134) are arranged in a first plane (P1) extending axially along and through (i.e., containing) the central axis of trocar (100). A second needle guide tube (154) and its needle entrance and exit ports (150, 152) are arranged in a second axially extending plane (P2) containing the central axis of trocar (100). Accordingly, the first and second suture paths defined by needle ports (150, 152) and needle guide tubes (154) intersect at the central axis. Knob (186) of latch ring (110) is arranged in a third axially extending plane (P3) containing the central axis. It will be understood that third plane (P3) may correspond to a midpoint of the circumferential path along which knob (186) travels when latch ring (110) rotates relative to the remainder of trocar (100).

In the present example, second plane (P2) is offset from first plane (P1) such that the first and second needle tubes (154) are positioned in a non-diametrically opposed relationship, and the resulting first and second suture paths lie in different planes. More specifically, in some examples second plane (P2) may be offset from first plane (P1) by approximately 17 degrees. Furthermore, in the present example third plane (P3) extends perpendicularly to first plane (P1) such that knob (186) is circumferentially offset from each of first needle guide tube (154) and insufflation port (134) by approximately 90 degrees. Accordingly, needle guide tubes (154), insufflation port (134), and latch ring knob (186) are circumferentially offset from one another in the present example. Additionally, knob (186) remains circumferentially offset from each needle guide tube (154) and insufflation port (134) throughout a full range of permissible rotation of latch ring (110) about the central axis of trocar (100). Such a configuration ensures unobstructed access to needle guide tubes (154) during use of trocar (100).

It will be appreciated that in other examples, axially extending planes (P1, P2, P3) may be arranged in various other configurations. In that regard, second plane (P2) containing second needle guide tube (154) and its needle entrance port (150) may be offset from first plane (P1) by greater than or less than 17 degrees. Additionally, third plane (P3) containing latch ring knob (186) may be non-perpendicular to first plane (P1). For instance, third plane (P3) may be oriented such that knob (186) is circumferentially offset from insufflation port (134) or first needle guide tube (154) by greater than or less than 90 degrees. Furthermore, while trocar (100) of the present example is shown and described as providing two suture paths oriented in a particular arrangement, each suture path being defined by a respective needle entrance port (150) and needle exit port (152), other versions of trocar (100) may be suitably configured to provide alternative quantities and arrangements of suture paths. For example, trocar (100) may be configured to provide three or more suture paths.

Figure 9:
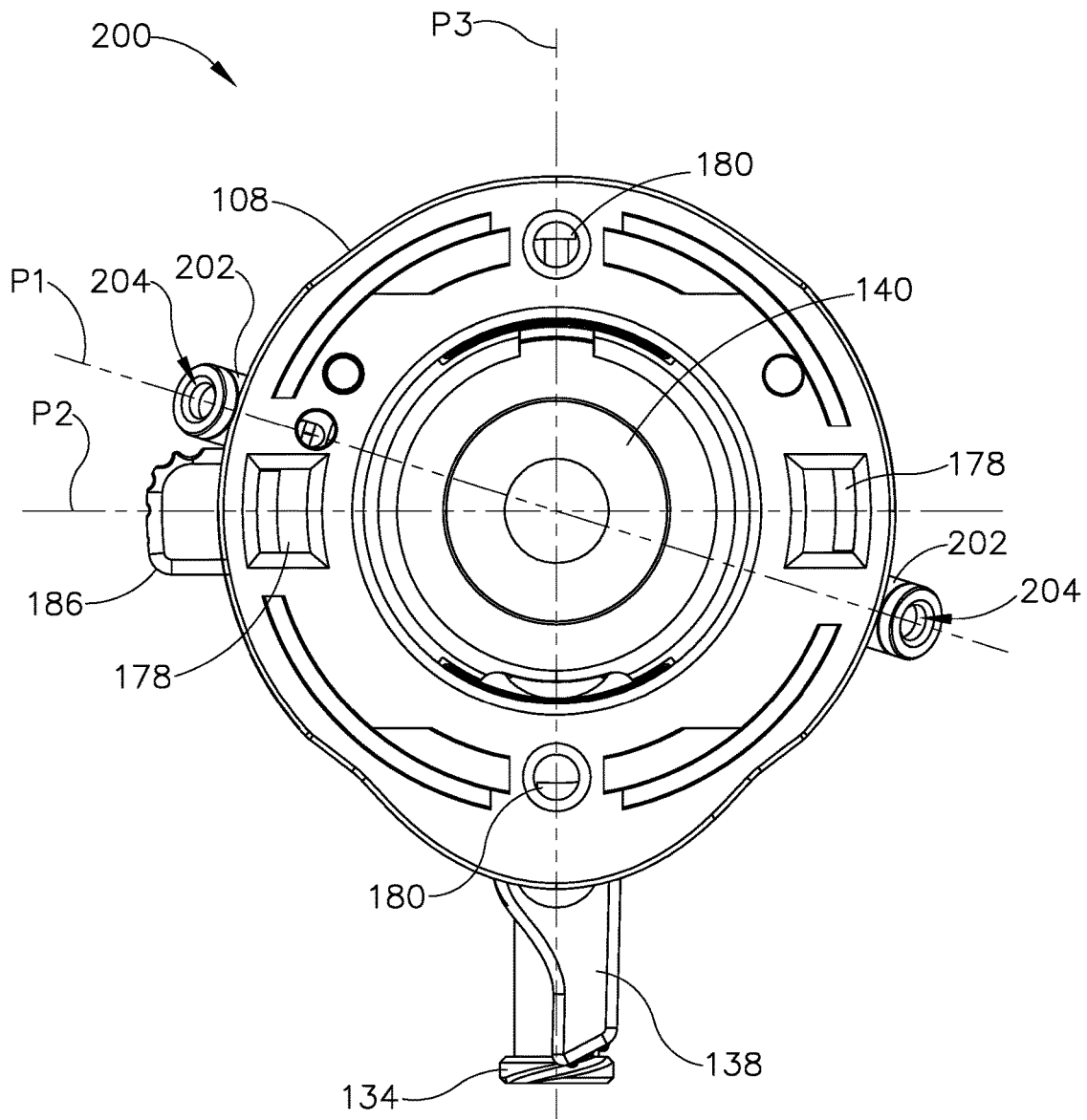
FIG. 9 depicts a top elevational view of another exemplary trocar.

B. Exemplary Trocar Having Needle Ports and Insufflation Port in Second Arrangement FIG. 9 shows another exemplary surgical access device in the form of trocar (200), for which like reference numerals refer to like features described above in connection with trocar (100). Trocar (200) is substantially similar to trocar (100) except as otherwise described below. In particular, trocar (200) includes a pair of needle guide tubes (202) and corresponding needle entrance ports (204) that are arranged in a diametrically opposing relationship along a first axially extending plane (P1) containing the central axis of trocar (200). A second axially extending plane (P2) extends through the central trocar axis and latch ring knob (186), and a third axially extending plane (P3) extends through the central trocar axis and insufflation port (134). In various examples, second plane (P2) may extend through a path endpoint or a path midpoint of knob (186).

In the present example, second plane (P2) extends perpendicularly to third plane (P3) such that latch ring knob (186) is circumferentially offset from insufflation port (134) by 90 degrees. Additionally, first plane (P1) is angularly offset from second plane (P2) and third plane (P3) such that needle guide tubes (202) and needle entrance ports (204) are circumferentially offset from knob (186) and insufflation port (134). In the present example, first plane (P1) is angularly offset from second plane (P2) by approximately 17 degrees. Alternative versions of trocar (200) may present angular offsets of first plane (P1) relative to second plane (P2) of greater than or less than 17 degrees.

C. Exemplary Trocar Having Needle Ports Arranged on Rotary Collar

During a suturing procedure for closing a tissue opening using a trocar having needle entrance and exit ports defining one or more suture paths, such as one or both of trocars (100, 200) described above, it may be desirable to adjust the rotational position of one or more of the suture paths about the trocar central axis in situ, without rotating the trocar as a whole relative to the patient. Such adjustment may be desirable, for example, to better accommodate certain anatomy of the patient and achieve a better "bite" of the tissue fascia being sutured. Exemplary trocar features described below enable such adjustment.

Figure 10:
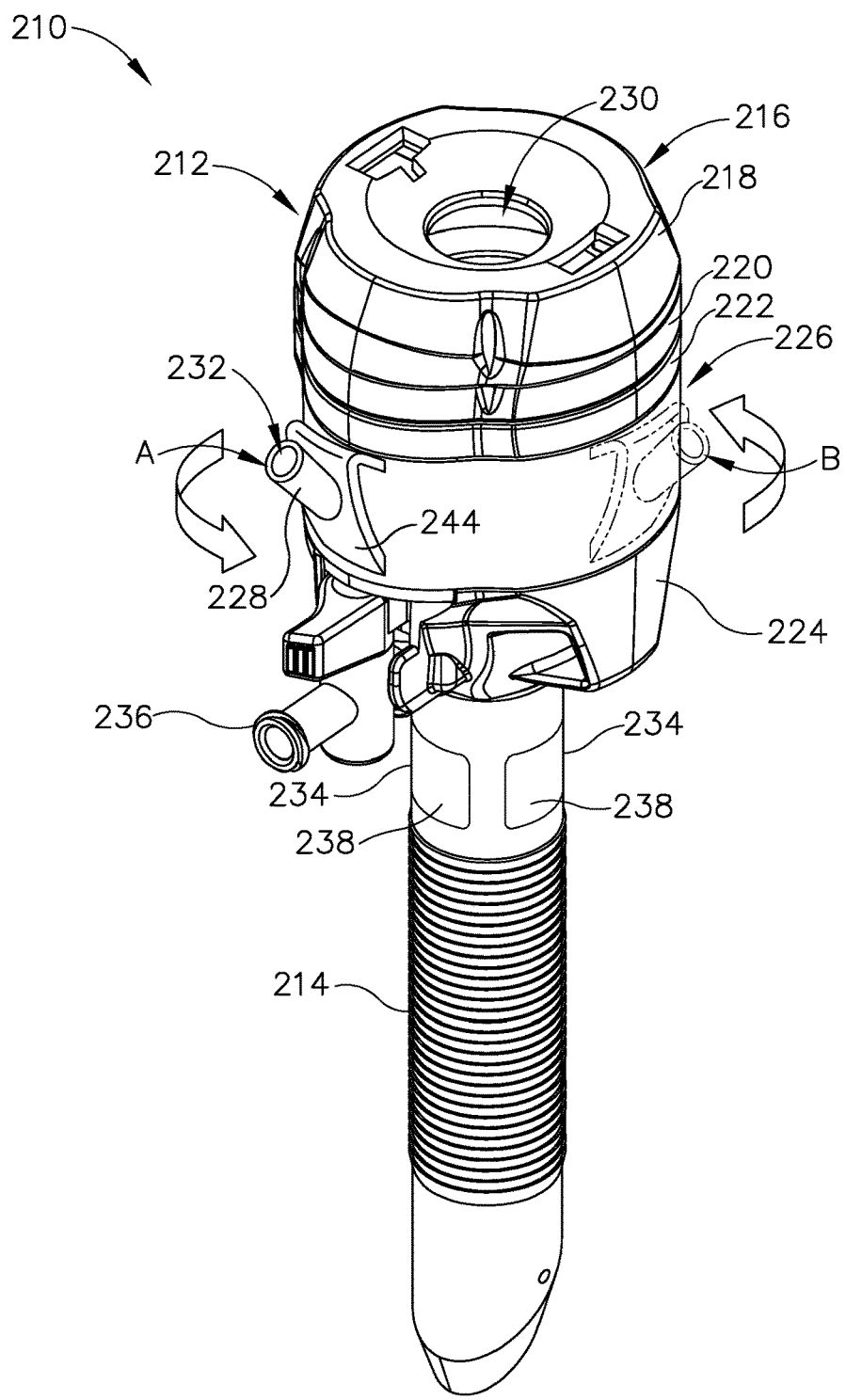
FIG. 10 depicts a perspective view of another exemplary trocar having a rotary collar.

FIG. 10 shows an exemplary trocar (210) configured to enable selective rotational adjustment of its suture paths about a central axis of trocar (210). Trocar (210) is similar to trocar (100) in that trocar (210) includes a housing assembly (212) and a cannula (214) coupled to and extending distally from housing assembly (212) along a trocar central axis. Housing assembly (212) includes a proximal housing (216) having a proximal housing head (218) and a proximal housing base (220), a housing cap plate (222), a latch ring (not shown) similar to latch ring (110), and a distal housing (224). The components of trocar (210) are substantially similar in structure and function to the corresponding components of trocar (100) described above, except as otherwise described below.

Unlike housing assembly (102) of trocar (100), housing assembly (212) of trocar (210) includes a rotary collar (226) arranged between housing cap plate (222) and distal housing (224). Rotary collar (226) supports a pair of needle guide tubes (228), each guide tube (228) defining a needle entrance port (232) that communicates with a working channel (230) of trocar (210). Rotary collar (226) is configured to enable selective rotational adjustment of one or both of needle guide tubes (228) and their respective suture paths about the trocar central axis relative to rotationally-fixed components of trocar (210), including a pair of needle exit ports (234) formed in cannula (214). For instance, in the present example needle guide tubes (228) are fixed relative to rotary collar (226), and rotary collar (226) is configured to rotate about the trocar central axis. Consequently, first and second needle guide tubes (228) rotate together about trocar central axis. In other examples, rotary collar (226) may be fixed relative to cannula (214) while first and second needle guide tubes (228), or other needle guide structures, are configured to rotate independently or dependently of one another about trocar central axis, for example along one or more circumferentially extending tracks (not shown) formed in rotary collar (226).

Rotary collar (226) is configured to rotate relative to cannula (214) between first and second end positions, as indicated by reference numerals (A, B) in FIG. 10. First and second end positions (A, B) are circumferentially offset from one another by any suitable degree, such as approximately 30-45 degrees, for example. Additionally, rotary collar (226) is mounted to trocar (210) such that when rotary collar (226) is in its first end position (A) a first needle guide tube (228) is circumferentially offset from insufflation port (236) by a selected degree, such as approximately 17 degrees. Accordingly, in an exemplary configuration in which rotary collar (226) rotates through a range of 45 degrees between first and second end positions (A, B), first needle guide tube (228) is movable from a first end position in which guide tube (228) is offset from insufflation port by 17 degrees, to a second end position in which needle guide tube (228) is offset from insufflation port (236) by 57 degrees. In various examples, trocar (210) may include one or more detent mechanisms or other rotation limiting mechanisms (not shown) configured to releasably retain rotary collar (226) in one or more predetermined rotational positions relative to cannula (214).

As shown in FIG. 10, needle exit ports (234) are formed in a proximal cylindrical portion of cannula (214). Each exit port (234) extends circumferentially about trocar central axis with a circumferential dimension sufficient to enable a corresponding needle guide tube (228) to align with needle exit port (234) throughout a full range of rotation of rotary collar (226) between its first and second end positions (A, B). Additionally, each needle exit port (234) is formed with an axial dimension sufficient to accommodate suture paths therethrough of various different suture path angles. In alternative examples, trocar (210) may include a plurality of needle exit ports arranged circumferentially about trocar central axis at locations corresponding to predetermined rotational positions of rotary collar (226). Each needle exit port (234) includes a pierceable seal (238) configured to assist in maintaining insufflation during a surgical procedure, similar to seals (162) of trocar (100). Each needle guide tube (228) may also include a pierceable seal (not shown), such as a seal cap (not shown) similar to seal caps (158) of trocar (100).

Figure 11:
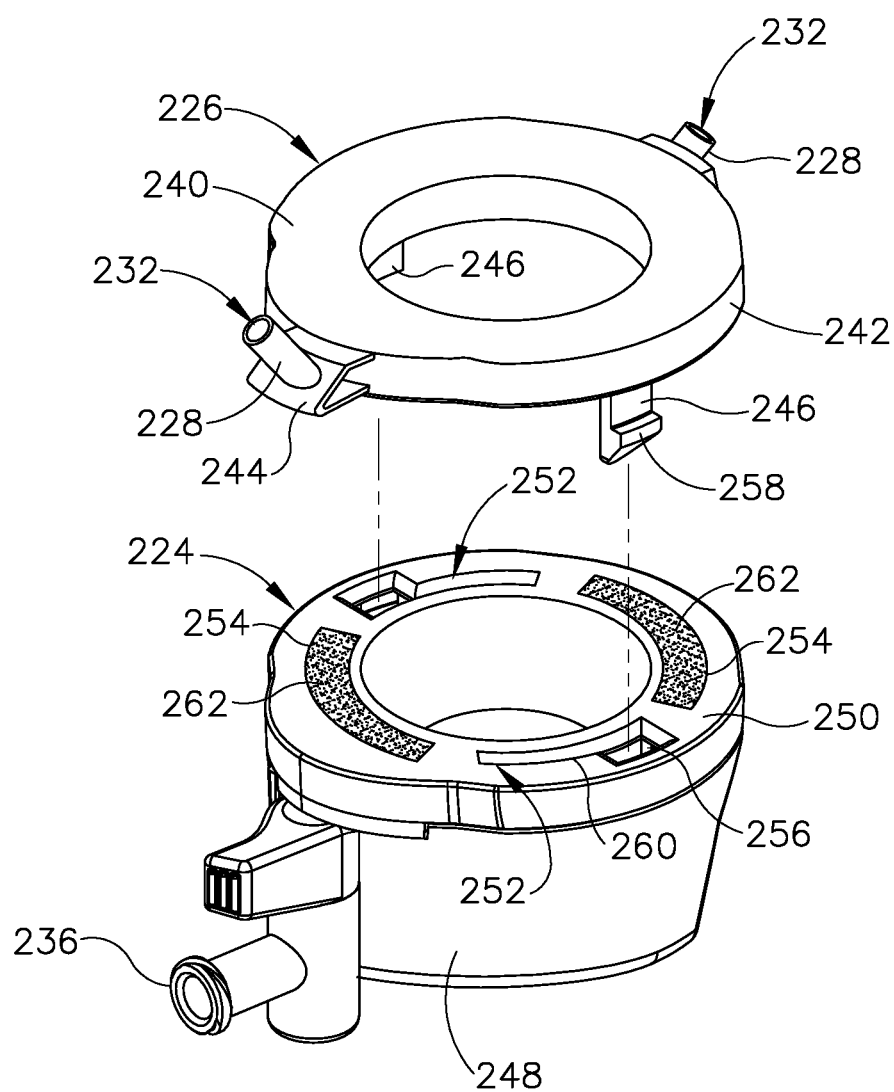
FIG. 11 depicts a disassembled perspective view of the rotary collar and a distal housing of the trocar of FIG. 10.

FIG. 11 shows additional details of exemplary features of rotary collar (226) and distal housing (224). Rotary collar (226) includes a generally annular body (240) and an outer sidewall (242) that supports needle guide tubes (228). Each needle guide tube (228) is supported by a shoulder element (244) projecting radially outwardly from annular body (240), and needle guide tubes (228) are arranged at diametrically opposed positions on annular body (240). In other examples, needle guide tubes (228) may be arranged in various other configurations, such as those described above in connection with trocars (100, 200). Additionally, needle guide tubes (228) and/or shoulder elements (244) may be omitted and replaced with needle guide structures of various other forms, such as structures integrated within annular body (240) of rotary collar (226). Rotary collar (226) further includes a pair of downwardly depending L-shaped legs (246) configured to couple rotary collar (226) with distal housing (224) and guide rotation of rotary collar (226) relative to distal housing (224), as described below. In the present example, legs (246) are diametrically opposed from one another and are spaced circumferentially equidistantly between needle guide tubes (228).

Distal housing (224) of the present example includes a generally annular body (248) having an upper wall (250). A pair of circumferentially extending slots (252) are arranged in upper wall (250) and are configured to receive downwardly depending legs (246) of rotary collar (226). A pair of circumferentially extending sealed openings (254) are also arranged in upper wall (250) and are configured to receive a suture passer needle (not shown) therethrough. Slots (252) and sealed openings (254) are arranged in a circumferentially alternating manner, such that each slot (252) is configured to align with a respective leg (246) and each sealed opening (254) is configured to align with the distal end of a respective needle guide tube (228). Each slot (252) has a radially enlarged opening (256) configured to receive a radially projecting distal foot (258) of the respective leg (246) when rotary collar (226) is assembled with distal housing (224). Each slot (252) further includes an elongate channel (260) extending circumferentially from enlarged opening (256) and configured to retain and guide legs (246) along a circumferential path as rotary collar (226) rotates relative to distal housing (224). A circumferential length of slot (252) defines the permissible rotational range of rotary collar (226) relative to distal housing (224), and may be suitably sized to provide any desired rotational range.

Each circumferentially extending sealed opening (254) is formed with a circumferential length sufficient to enable alignment of the distal end of a respective needle guide tube (228) with sealed opening (254) throughout the entire permissible range of rotation of rotary collar (226) relative to distal housing (224). Each sealed opening (254) is provided with a pierceable seal (262) configured to be pierced by a suture passer needle directed distally through the respective needle guide tube (228). In various examples, each pierceable seal (262) may include a circumferentially extending slit (not shown) configured to facilitate insertion of a suture passer needle distally through pierceable seal (262), and rotation of rotary collar (226) relative to distal housing (224) while suture passer needle extends through pierceable seal (262). Each sealed opening (254) is configured to direct a suture passer needle into working channel (230) and toward a respective needle exit port (234) on cannula (214). Additionally, each sealed opening (254) is formed with a radial dimension sufficient to accommodate suture paths therethrough of various different suture path angles.

Each of the exemplary trocars (100, 200, 210) described above is configured to be implemented as a suture guide mechanism for directing suture guide needles, and suture thread carried by the suture guide needles, distally therethrough and into tissue at predetermined suture path angles for suturing closed an opening formed in a patient by the trocar cannula. Any of trocars (100, 200, 210) may be implemented in connection with the general steps of the exemplary suturing procedure disclosed in U.S. App. No. 15/637,683, filed on Jun. 29, 2017, incorporated by reference above, for example. Additionally, the teachings presented herein with respect to trocars (100, 200, 210) may be further combined with various teachings of any one or more of the following: U.S. App. No. 15/637,690, entitled "Needle Guide Instrument with Traverse Suture Capture Feature," filed on even date herewith, published as U.S. Pub. No. 2019/0000443 on Jan. 3, 2019, the disclosure of which is incorporated by reference herein; U.S. App. No. 15/637,702, entitled "Suture Grasping Instrument," filed on even date herewith, published as U.S. Pub. No. 2019/0000440 on Jan. 3, 2019, the disclosure of which is incorporated by reference herein; U.S. App. No. 15/637,712, entitled "Suture Passing Instrument with Puncture Site Identification Feature," filed on even date herewith, published as U.S. Pub. No. 2019/0000444 on Jan. 3, 2019, the disclosure of which is incorporated by reference herein; U.S. App. No. 15/637,696, entitled "Trocar Obturator with Transverse Needle Ports," filed on even date herewith, published as U.S. Pub. No. 2019/0000506 on Jan. 3, 2019, the disclosure of which is incorporated by reference herein; U.S. App. No. 15/637,707, entitled "Surgical Port with Wound Closure Channels," filed on even date herewith, published as U.S. Pub. No. 2019/0000441 on Jan. 3, 2019, the disclosure of which is incorporated by reference herein; U.S. App. No. 15/637,735, entitled "Trocar Obturator with Detachable Rotary Tissue Fastener," filed on even date herewith, published as U.S. Pub. No. 2019/0000502 on Jan. 3, 2019, the disclosure of which is incorporated by reference herein; U.S. App. No. 15/637,778, entitled "Method of Suturing a Trocar Patch Incision," filed on even date herewith, published as U.S. Pub. No. 2019/0000496 on Jan. 3, 2019, the disclosure of which is incorporated by reference herein; and/or other patents and patent application publications incorporated by reference herein.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical access device, comprising: (a) a cannula having a proximal end, a distal end, and a cannula lumen extending therebetween (b) a housing assembly coupled to the proximal end of the cannula, wherein the housing assembly defines a housing interior in communication with the cannula lumen; (c) a working channel extending from a proximal end of the surgical access device to a distal end of the surgical access device along a central axis thereof, wherein the working channel is defined by the cannula lumen and the housing interior, wherein the working channel is configured to receive a surgical instrument therethrough; (d) an insufflation port configured to direct insufflation fluid into the working channel; (e) a first needle port that opens to the working channel through a first side portion of the surgical access device, wherein the first needle port is diametrically opposed from the insufflation port; and (f) a second needle port that opens to the working channel through a second side portion of the surgical access device, wherein each of the first and second needle ports is configured to direct a suture passer needle through the surgical access device, across the working channel, at an oblique angle relative to the central axis.

Example 2

The surgical access device of Example 1, wherein the second needle port is circumferentially offset from the insufflation port.

Example 3

The surgical access device of Example 2, wherein the second needle port is circumferentially offset from the insufflation port by at least 17 degrees.

Example 4

The surgical access device of any one or more of the preceding Examples, wherein the housing assembly includes a proximal housing and a latch ring configured to releasably couple the proximal housing with the cannula, wherein the latch ring includes a user engagement feature that is actuatable to release the proximal housing from the cannula, wherein the user engagement feature is circumferentially offset from the insufflation port throughout a full range of permissible motion of the user engagement feature.

Example 5

The surgical access device of Example 4, wherein the latch ring is movable to a position in which the user engagement feature is circumferentially offset from the insufflation port by at least 90 degrees.

Example 6

The surgical access device of any one or more of Examples 4 through 5, wherein the user engagement feature comprises an outwardly projecting knob.

Example 7

The surgical access device of any one or more of Examples 4 through 6, wherein the latch ring is rotatable about the central axis relative to the proximal housing.

Example 8

The surgical access device of any one or more of the preceding Examples, wherein the cannula includes a proximal hub configured to couple with the housing assembly, wherein the first and second needle ports extend through the proximal hub.

Example 9

The surgical access device of any one or more of the preceding Examples, wherein the first needle port comprises a first needle entrance port and the second needle port comprises a second needle entrance port, wherein the surgical access device further comprises a first needle exit port arranged distally of the first needle entrance port, and a second needle exit port arranged distally of the second needle entrance port, wherein the first needle entrance port and the first needle exit port together define a first suture path extending obliquely across the central axis of the surgical access device, wherein the second needle entrance port and the second needle exit port together define a second suture path extending obliquely across the central axis of the surgical access device.

Example 10

The surgical access device of Example 9, wherein the cannula includes a proximal hub and a cylindrical portion extending distally from the proximal hub, wherein the first and second needle exit ports open to the working channel through the cylindrical portion.

Example 11

The surgical access device of any one or more of Examples 9 through 10, wherein the first and second needle entrance ports and the first and second needle exit ports are arranged such that the first and second suture paths extend through the central axis of the surgical access device.

Example 12

The surgical access device of any one or more of Examples 9 through 11, further comprising a first needle guide structure configured to guide a suture passer needle through the first needle entrance port and along the first suture path, and a second needle guide structure configured to guide a suture passer needle through the second needle entrance port and along the second suture path.

Example 13

The surgical access device of Example 12, wherein the first and second needle guide structures comprise first and second needle guide tubes.

Example 14

The surgical access device of any one or more of Examples 9 through 13, wherein the first needle exit port is diametrically opposed from the first needle entrance port, wherein the second needle exit port is diametrically opposed from the second needle entrance port.

Example 15

The surgical access device of any of Examples 9 through 14, wherein the first needle entrance port, the first needle exit port, and the insufflation port lie in a plane extending axially through the surgical access device along the central axis thereof.

Example 16

A surgical access device, comprising: (a) a cannula having a proximal hub, a distal tip, and a cannula lumen extending therebetween; (b) a housing assembly coupled to the proximal hub of the cannula, wherein the housing assembly defines a housing interior in communication with the cannula lumen; (c) a working channel extending from a proximal end of the surgical access device to a distal end of the surgical access device along a central axis thereof, wherein the working channel is defined by the cannula lumen and the housing interior, wherein the working channel is configured to receive a surgical instrument therethrough; (d) an insufflation port configured to direct insufflation fluid into the working channel; and (e) a needle port that opens to the working channel through the proximal hub of the cannula, wherein the needle port is diametrically opposed from the insufflation port, wherein the needle port is configured to direct a suture passer needle through the surgical access device, across the working channel, at an oblique angle relative to the central axis.

Example 17

The surgical access device of Example 16, further comprising a second needle port that opens to the working channel through the proximal hub of the cannula, wherein the second needle port is circumferentially offset from the insufflation port.

Example 18

A surgical access device, comprising: (a) a cannula having a proximal end, a distal end, and a cannula lumen extending therebetween; (b) a housing assembly coupled to the proximal end of the cannula, wherein the housing assembly defines a housing interior in communication with the cannula lumen; (c) a working channel extending from a proximal end of the surgical access device to a distal end of the surgical access device along a central axis thereof, wherein the working channel is defined by the cannula lumen and the housing interior, wherein the working channel is configured to receive a surgical instrument therethrough; (d) an insufflation port configured to direct insufflation fluid into the working channel; (e) a first needle entrance port that opens to the working channel through a side portion of the surgical access device; (f) a first needle exit port that opens to the working channel through a side portion of the surgical access device, wherein the first needle exit port communicates with the first needle entrance port to define a first needle channel configured to guide a suture passer needle through the surgical access device, across the working channel, at an oblique angle relative to the central axis; (g) a second needle port that opens to the working channel through a side portion of the surgical access device; and (h) a second needle exit port that opens to the working channel through a side portion of the surgical access device, wherein the second needle exit port communicates with the second needle entrance port to define a second needle channel configured to guide a suture passer needle through the surgical access device, across the working channel, at an oblique angle relative to the central axis, wherein at least one of the first or second needle entrance ports and its respective needle exit port lie in an axial plane extending axially through the surgical access device along the central axis thereof, wherein the axial plane is offset from the insufflation port.

Example 19

The surgical access device of Example 18, wherein the first needle entrance port, the first needle exit port, and the insufflation port lie in a first axial plane extending axially through the surgical access device along the central axis thereof, wherein the second needle entrance port and the second needle exit port lie in a second axial plane extending axially through the surgical access device along the central axis, wherein the second axial plane is offset from the first axial plane.

Example 20

The surgical access device of Example 18, wherein each of the first needle entrance port and the second needle entrance port is circumferentially offset from the insufflation port.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A surgical access device, comprising:
   (a) a cannula having a proximal end, a distal end, and a cannula lumen extending therebetween;
   (b) a housing assembly coupled to the proximal end of the cannula, wherein the housing assembly defines a housing interior in communication with the cannula lumen, wherein the housing assembly includes a proximal housing that is selectively releasable relative to the cannula;
   (c) a working channel extending from a proximal end of the surgical access device to a distal end of the surgical access device along a central axis thereof, wherein the working channel is defined by the cannula lumen and the housing interior, wherein the working channel is configured to receive a surgical instrument therethrough;
   (d) an insufflation port configured to direct insufflation fluid into the working channel;
   (e) a first needle port that opens to the working channel through a first side portion of the surgical access device, wherein the first needle port is diametrically opposed from the insufflation port; and
   (f) a second needle port that opens to the working channel through a second side portion of the surgical access device,
   wherein each of the first and second needle ports is configured to direct a suture passer needle through the surgical access device, across the working channel, at an oblique angle relative to the central axis.

2. The surgical access device of claim 1, wherein the second needle port is circumferentially offset from the insufflation port.

3. The surgical access device of claim 2, wherein the second needle port is circumferentially offset from the insufflation port by at least 17 degrees.

4. The surgical access device of claim 1, wherein the housing assembly further includes a latch ring configured to releasably couple the proximal housing with the cannula, wherein the latch ring includes a user engagement feature that is actuatable to release the proximal housing from the cannula, wherein the user engagement feature is circumferentially offset from the insufflation port throughout a full range of permissible motion of the user engagement feature.

5. The surgical access device of claim 4, wherein the latch ring is movable to a position in which the user engagement feature is circumferentially offset from the insufflation port by at least 90 degrees.

6. The surgical access device of claim 4, wherein the user engagement feature comprises an outwardly projecting knob.

7. The surgical access device of claim 4, wherein the latch ring is rotatable about the central axis relative to the proximal housing.

8. The surgical access device of claim 1, wherein the cannula includes a proximal hub configured to couple with the housing assembly, wherein the first and second needle ports extend through the proximal hub.

9. The surgical access device of claim 1, wherein the first needle port comprises a first needle entrance port and the second needle port comprises a second needle entrance port, wherein the surgical access device further comprises a first needle exit port arranged distally of the first needle entrance port, and a second needle exit port arranged distally of the second needle entrance port, wherein the first needle entrance port and the first needle exit port together define a first suture path extending obliquely across the central axis of the surgical access device, wherein the second needle entrance port and the second needle exit port together define a second suture path extending obliquely across the central axis of the surgical access device.

10. The surgical access device of claim 9, wherein the cannula includes a proximal hub and a cylindrical portion extending distally from the proximal hub, wherein the first and second needle exit ports open to the working channel through the cylindrical portion.

11. The surgical access device of claim 9, wherein the first and second needle entrance ports and the first and second needle exit ports are arranged such that the first and second suture paths extend through the central axis of the surgical access device.

12. The surgical access device of claim 9, further comprising a first needle guide structure configured to guide a suture passer needle through the first needle entrance port and along the first suture path, and a second needle guide structure configured to guide a suture passer needle through the second needle entrance port and along the second suture path.

13. The surgical access device of claim 12, wherein the first and second needle guide structures comprise first and second needle guide tubes.

14. The surgical access device of claim 9, wherein the first needle exit port is diametrically opposed from the first needle entrance port, wherein the second needle exit port is diametrically opposed from the second needle entrance port.

15. The surgical access device of claim 9, wherein the first needle entrance port, the first needle exit port, and the insufflation port lie in a plane extending axially through the surgical access device along the central axis thereof.

16. A surgical access device, comprising:
   (a) a cannula having a proximal hub, a cylindrical body extending distally from the proximal hub, a distal tip, and a cannula lumen, wherein the proximal hub has a different diameter than the cylindrical body;
   (b) a housing assembly coupled to the proximal hub of the cannula, wherein the housing assembly defines a housing interior in communication with the cannula lumen;
   (c) a working channel extending from a proximal end of the surgical access device to a distal end of the surgical access device along a central axis thereof, wherein the working channel is defined by the cannula lumen and the housing interior, wherein the working channel is configured to receive a surgical instrument therethrough;

(d) an insufflation port configured to direct insufflation fluid into the working channel; and (e) a needle port that opens to the working channel through a side portion of the proximal hub of the cannula, wherein the needle port is diametrically opposed from the insufflation port, wherein the needle port is configured to direct a suture passer needle through the surgical access device, across the working channel, at an oblique angle relative to the central axis.

17. The surgical access device of claim 16, further comprising a second needle port that opens to the working channel through a side portion of the proximal hub of the cannula, wherein the second needle port is circumferentially offset from the insufflation port.

18. A surgical access device, comprising:
(a) a cannula having a proximal hub defining a proximal end, a distal end, and a cannula lumen extending therebetween;
(b) a housing assembly coupled to the proximal hub of the cannula, wherein the housing assembly defines a housing interior in communication with the cannula lumen;
(c) a working channel extending from a proximal end of the surgical access device to a distal end of the surgical access device along a central axis thereof, wherein the working channel is defined by the cannula lumen and the housing interior, wherein the working channel is configured to receive a surgical instrument therethrough;
(d) an insufflation port configured to direct insufflation fluid into the working channel through the proximal hub;
(e) a first needle entrance port that opens to the working channel through a side portion of the proximal hub;

(f) a first needle exit port that opens to the working channel through a side portion of the surgical access device, wherein the first needle exit port communicates with the first needle entrance port to define a first needle channel configured to guide a suture passer needle through the surgical access device, across the working channel, at an oblique angle relative to the central axis;

(g) a second needle entrance port that opens to the working channel through a side portion of the proximal hub; and (h) a second needle exit port that opens to the working channel through a side portion of the surgical access device, wherein the second needle exit port communicates with the second needle entrance port to define a second needle channel configured to guide a suture passer needle through the surgical access device, across the working channel, at an oblique angle relative to the central axis, wherein at least one of the first or second needle entrance ports and its respective needle exit port lie in an axial plane extending axially through the surgical access device along the central axis thereof, wherein the axial plane is offset from the insufflation port.

19. The surgical access device of claim 18, wherein the first needle entrance port, the first needle exit port, and the insufflation port lie in a first axial plane extending axially through the surgical access device along the central axis thereof, wherein the second needle entrance port and the second needle exit port lie in a second axial plane extending axially through the surgical access device along the central axis, wherein the second axial plane is offset from the first axial plane.

20. The surgical access device of claim 18, wherein each of the first needle entrance port and the second needle entrance port is circumferentially offset from the insufflation port.

* * * * *